United States Patent [19]

Davies et al.

[11] Patent Number: 5,801,249

[45] Date of Patent: Sep. 1, 1998

[54] CHIRAL AUXILIARIES

[75] Inventors: Stephen Graham Davies, Oxford; Mario Eugenio Cosamino Polywka, Oxon; Hitesh Jayantilal Sanganee, London, all of Great Britain

[73] Assignee: Oxford Asymmetry International plc, Abingdon, United Kingdom

[21] Appl. No.: 663,258

[22] PCT Filed: Dec. 28, 1994

[86] PCT No.: PCT/GB94/02826

§ 371 Date: Jun. 24, 1996

§ 102(e) Date: Jun. 24, 1996

[87] PCT Pub. No.: WO95/18112

PCT Pub. Date: Jul. 6, 1995

[30] Foreign Application Priority Data

Dec. 24, 1993 [GB] United Kingdom ............ 9326432

[51] Int. Cl.[6] ............................................ C07D 263/20
[52] U.S. Cl. ............................................ 548/229; 548/230
[58] Field of Search ........................... 548/229, 188, 548/230

[56] References Cited

U.S. PATENT DOCUMENTS 5,461,162  10/1995  Ho .................................... 548/188

FOREIGN PATENT DOCUMENTS 0 457 469  11/1991  European Pat. Off. .
0 471 201  2/1992  European Pat. Off. .

*Primary Examiner*—Robert Gerstl
*Attorney, Agent, or Firm*—Bacon & Thomas

[57] ABSTRACT

This invention relates to novel compounds of general formula (I):

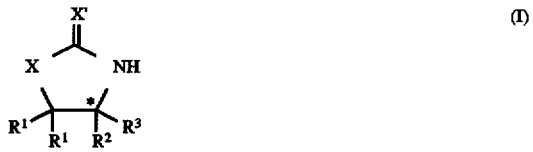

wherein the two $R^1$ groups are identical lower alkyl groups or together form a lower alkylene group; $R^2$ and $R^3$ are both different and are selected from hydrogen atoms or organic groups; X and X', which may be the same or different, are selected from O, S and NR, where R represents an organic group; and the asterisk denotes that the configurations of $R^2$ and $R^3$ are such that the compound (I) is in substantially enantiomerically pure 4R- or 4S-form. The compounds are useful chiral auxiliaries to which a wide range of, for example, acyl groups containing prochiral centers may be readily and reversibly coupled to the 3-position amino group.

10 Claims, No Drawings

CHIRAL AUXILIARIES

This invention relates to new chiral auxiliaries and derivatives thereof useful in the synthesis of chiral molecules, in particular to new chiral auxiliaries containing an oxazolidinone ring structure or a thia or aza analogue thereof.

The use of chiral auxiliaries in the selective synthesis of single enantiomers of chiral molecules is now well known—see, for example, EP-A-0457469 and the references described therein. Such auxiliaries typically comprise (i) a reactive part carrying or to which may be coupled a moiety having a prochiral centre, and (ii) a chiral part which influences the stereochemical course of reactions at the prochiral centre, thereby encouraging the generation of substantially enantiomerically pure products. The auxiliary is preferably such that the desired single enantiomeric product can thereafter be uncoupled and recovered, with simultaneous regeneration of the reactive part of the auxiliary, thereby permitting a succession of subsequent sequences of coupling, stereoselective synthesis and uncoupling reaction stages using the same auxiliary.

A representative class of auxiliaries currently used in this way comprises 4-monosubstituted oxazolidin-2-ones of formula

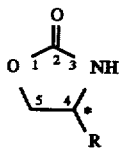

(where R represents an organic group and the asterisk denotes that this group is predominantly in the R- or S-configuration such that the compound (A) is in substantially enantiomerically pure form). Here the 3-position amino group represents the reactive part (i) to which may be coupled a moiety, e.g. an acyl group, having a prochiral centre; the group R at the 4-position represents the chiral part (ii) which will direct the stereochemical course of reactions at such a prochiral centre.

An important requirement of such auxiliaries is that their basic structure should be substantially completely stable under the various reaction conditions employed, in particular that the structure should not be degraded under the conditions used for uncoupling of the desired stereoselective product. Similarly it is critical that uncoupling may be effected under conditions which are sufficiently mild not to induce racemisation of the desired substantially enantiomerically pure product.

A problem encountered with the above-described auxiliaries (A) is that the oxazolidinone ring may not exhibit sufficient stability during uncoupling reactions. Thus, for example, removal of an acyl group from the 3-position amino group, e.g. by acid- or base-catalysed hydrolysis, may also be accompanied by substantial degradation of the oxazolidinone ring, as illustrated in the following sequence:

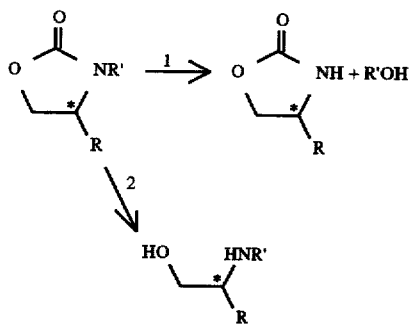

(where R and the asterisk are as hereinbefore defined and R' represents an acyl group). In this sequence path 1 is the desired uncoupling reaction (product cleavage) and path 2 represents unwanted degradation of the auxiliary (oxazolidinone cleavage). It will be appreciated that such degradation reduces both the yield of the desired product and the level of recovery of the auxiliary and thus has substantial adverse effects on operating costs, particularly for large-scale processes.

This problem is currently ameliorated by using hydroperoxides as cleavage agents in conjunction with oxazolidinone chiral auxiliaries, these directing the cleavage reaction predominantly along the desired product cleavage path 1. Such peroxide-based materials are hazardous to use, however, and there is thus a continuing need for chiral auxiliaries with improved stability under e.g. hydrolysing conditions and which permit stereoselective syntheses involving a wide range of prochiral centre-containing moieties.

The present invention is based on our finding that 4-asymmetrically substituted oxazolidin-2-ones and thia and aza analogues thereof may be stabilised against unwanted oxazolidinone cleavage if the 5-position of the ring is symmetrically disubstituted, whereby a wide range of e.g. acyl groups containing prochiral centres may be readily and reversibly coupled to the 3-position amino group. Most surprisingly, the presence of such substituents at the 5-position does not appear to affect the stereochemical bias exerted on such a prochiral centre by the group or groups at the 4-position which create the chiral part of the auxiliary.

Thus according to one aspect of the present invention there are provided compounds of general formula (I)

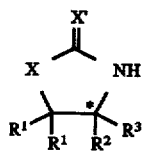

(where the two $R^1$ groups are identical lower alkyl groups or together form a lower alkylene group; $R^2$ and $R^3$ are both different and are selected from hydrogen atoms and organic groups; X and X', which may be the same or different, are selected from O, S and NR, where R represents an organic group; and the asterisk denotes that the configurations of $R^2$ and $R^3$ are such that the compound (I) is in substantially enantiomerically pure 4R- or 4S- form).

The term substantially enantiomerically pure as used herein denotes compounds containing at least 80%, advantageously at least 90%, and preferably at least 95% of the desired enantiomer.

Where the groups $R^1$ in formula (I) represent lower alkyl groups these may, for example, contain 1–10, e.g. 1–6 carbon atoms, as in methyl, ethyl, n-propyl, isopropyl, n-butyl, sec-butyl and tert-butyl groups. When the $R^1$ groups together represent a lower alkylene group this may, for example, contain 3–10 carbon atoms, e.g. as in trimethylene, tetramethylene, pentamethylene and hexamethylene groups. In a preferred class of compounds according to the invention both $R^1$ groups represent methyl.

The group $R^2$ can be selected from a wide range of organic groupings, including, for example, aliphatic, cycloaliphatic, araliphatic and aromatic groups, e.g. containing up to 20 carbon atoms and optionally carrying one or more substituents. $R^2$ may thus, for example, represent a group selected from $C_{1-10}$ alkyl such as methyl or ethyl; $C_{2-10}$ alkenyl such as vinyl or propenyl; $C_{3-10}$ cycloalkyl—$C_{1-4}$ alkyl such as cyclopentylmethyl; $C_{6-12}$ aryl—$C_{1-4}$ alkyl such as benzyl; $C_{6-12}$ aryl such as phenyl; and substituted versions of any of the preceding groups.

Since compounds of formula (I) may be derived from α-amino acids, one useful category of $R^2$ groups include the α-substituents of both natural and unnatural α-amino acids, for example methyl, isopropyl, isobutyl, sec-butyl, hydroxymethyl, 1-hydroxyethyl, mercaptomethyl, carboxymethyl, 2-carboxyethyl, carbamoylmethyl, 2-carbamoylethyl, 2-(methylthio)ethyl, 4-aminobutyl, benzyl, p-hydroxybenzyl, indol-3-ylmethyl, imidazol-4-ylmethyl or 3-guanidinopropyl.

One preferred category of $R^2$ groups may be represented by the formula

(where P represents an organic group, e.g. as defined above for $R^2$, especially a hydroxyl protecting group or a polymeric group).

Representative hydroxyl protecting groups include etherifying groups such as aralkyl (e.g. arylmethyl such as benzyl, p-nitrobenzyl or trityl) or hydrocarbylsilyl (e.g. trialkylsilyl such as trimethylsilyl or t-butyldimethylsilyl) and esterifying groups, for example acyl groups such as alkanoyl (e.g. acetyl or pivaloyl), alkenoyl (e.g. allylcarbonyl), aroyl (e.g. p-nitrobenzoyl), alkoxycarbonyl (e.g. t-butoxycarbonyl), haloalkoxycarbonyl (e.g. 2,2,2-trichloroethoxycarbonyl), aralkoxycarbonyl (e.g. benzyloxycarbonyl or p-nitrobenzyloxycarbonyl) or alkenyloxycarbonyl (e.g. allyloxycarbonyl).

Where P represents a polymer this may, for example, be an insoluble polymer, for example a crosslinked polysaccharide (e.g. a crosslinked agarose such as cepharose or a crosslinked dextran such as cephadex) or, more preferably, a divinylbenzene-crosslinked polystyrene system. The use of such insolubilised polymers, e.g. in bead form, as support systems for reagents is well known in the art.

$R^3$ preferably represents a hydrogen atom but may also represent an organic group, e.g. as hereinbefore described for $R^2$, with the proviso that $R^2$ and $R^3$ must be different.

R may, for example, be an organic group as described above for $R^2$.

The first stage in the use of compounds of formula (I) as chiral auxiliaries will normally comprise the introduction of a prochiral centre-containing substituent at the 3-position of the ring. Most commonly this substituent will be an acyl group, which may be represented by the formula

where $R^4$ is an organic group, e.g. which is a prochiral precursor for a desired chiral moiety. Such groups may be introduced by, for example, reaction of a compound (I) with an acylating agent of formula (II)

L.CO.R$^4$     (II)

where $R^4$ is as defined above and L represents a leaving group, e.g. a halogen atom such as chlorine or bromine. Reaction of acyl halides of formula (II) is preferably carried out in the presence of a strong base, e.g. a metal alkyl such as n-butyl lithium.

Such acylation of compounds of formula (I) leads to the formation of compounds of formula (III)

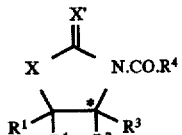

(where $R^1$, $R^2$, $R^3$, $R^4$, X, X' and the significance of the asterisk are as hereinbefore defined), which compounds constitute a further feature of the invention.

A wide range of $R^4$ groups may be present in the compounds of formula (III), for example aliphatic, cycloaliphatic, araliphatic and aromatic groups, e.g. alkyl and alkenyl groups containing up to 10 carbon atoms such as ethyl, propyl or propenyl, $C_{6-10}$ aryl—$C_{1-4}$ alkyl groups such as benzyl or phenethyl, and $C_{6-20}$ aryl groups such as phenyl or biphenyl groups. A variety of highly stereoselective reactions may be carried out on such compounds of formula (III), depending on factors such as the nature and position of the prochiral centre in the chosen $R^4$ group. Such reactions constitute a further feature of the invention.

In an important sub-class of compounds of formula (III) the $R^4$ group contains a terminal methylene group attached to the carbonyl group, so that the N-substituent may be written as

where $R^5.CH_2$ corresponds to a group $R^1$ as hereinbefore defined. Such methylene groups constitute prochiral centres at which it is possible to effect asymmetric substitution with a high degree of stereoselectivity, e.g. by reaction with an electrophile.

Sources of electrophiles which may be used in such reactions include, for example, alkyl and aralkyl halides, epoxides, aldehydes and ketones. The starting compound (III) is preferably reacted with a strong base capable of promoting enolisation of the side chain—$CO.CH_2$—group (e.g. a Group IA, IIA or IIIA metal alkyl, metal alkyl halide, metal alkyl trifluoroacetate or metal alkylamine such as lithium diisopropylamide), either during or, more preferably, before reaction with the source of electrophile. The reactions with the base and electrophile are preferably carried out in an inert solvent, e.g. a cyclic ether such as tetrahydrofuran, at a temperature of 0° C. or less, if desired under an inert atmosphere, e.g. of nitrogen.

Compounds of formula (III) in which $R^4$ represents a 1-alkenyl group, by virtue of being α, β-unsaturated ketones, may be subjected to Michael addition by reaction with a wide range of nucleophiles, e.g. Grignard reagents, malonic esters, acetoacetic esters, amines and derivatised amides etc., leading, where the 2-position of the alkenyl group is prochiral, to formation of substantially enantiomerically pure products. Such reactions are preferably carried out in an inert solvent at a temperature of 0° C. or less, if desired under an inert atmosphere, and preferably in the presence of a base such as an alkali metal alkoxide or a tertiary amine.

Compounds of formula (III) in which $R^4$ represents a 1-alkenyl group may also be subjected to stereoselective Diels-Alder reactions with appropriate conjugated dienes such as 1,3-butadiene, e.g. using thermal or Lewis acid catalysis.

Compounds of formula (III) in which $R^4$ is an aryl group may be subjected to a variety of stereoselective reactions in accordance with the invention. Thus, for example, a compound (III) in which $R^4$ is a substituted phenyl group may be subjected to a Birch reduction to yield a compound in which $R^4$ is a corresponding 2,5-cyclohexadienyl group, yielding this product in substantially enantiomerically pure form when the ring substitution pattern is such that a chiral centre is created at the 1-position of the cyclohexadienyl group. The invention may also be useful in the synthesis of individual atropisomers of e.g. compounds in which $R^2$ is an appropriately substituted biphenyl group.

After completion of the desired stereoselective asymmetric synthesis or syntheses the resulting product may be reacted to cleave the exocyclic nitrogen-carbon bond in order to release the desired product containing the newly created chiral centre and to regenerate the auxiliary of formula (I). Such cleavage may be effected by, for example, acid or base catalysed hydrolysis, e.g. using an alkali metal hydroxide such as lithium hydroxide in an aqueous/organic solvent system such as aqueous tetrahydrofuran, to yield a carboxylic acid or carboxylate salt corresponding to the chiral side chain and carbonyl group. Oxidative cleavage, e.g. with hydrogen peroxide, may similarly give a carboxylic acid, while hydrolytic cleavage using bases such as alkali metal alkoxides or aralkoxides (e.g. lithium benzyloxide) may be used to give corresponding alkyl or aralkyl carboxylate esters. Reductive cleavage, e.g. using a metal hydride reducing agent such as lithium aluminium hydride, may also be employed, yielding an alcohol grouping in place of the carbonyl group.

The regenerated chiral auxiliary of formula (I) may be recovered, reacylated, e.g. by reaction with a compound of formula (II) as hereinbefore described, and used in further asymmetric syntheses. It will be appreciated that such recovery and reprocessing of an auxiliary according to the invention are rendered particularly easy where the auxiliary is attached to a polymer support, e.g. where $R^2$ in formula (I) is a group

—CH₂OP where P represents a polymer.

The chiral auxiliaries of the invention may be prepared by any convenient method. Thus, for example, a substantially enantiomerically pure carboxyl-protected α-amino acid derivative having the formula (IV)

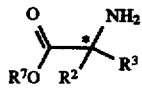  (IV)

(where R, $R^3$ and the asterisk have the above-defined meanings and $R^7$ is a carboxyl protecting group) or, more preferably, an acid addition salt thereof such as the hydrochloride may be reacted with two equivalents of a Grignard reagent $R^1MgX$ (where $R^1$ is as hereinbefore defined and X represents a halogen atom such as chlorine, bromine or iodine), e.g. in an aprotic organic solvent, for example an ether such as diethyl ether, to yield a compound of formula (V)

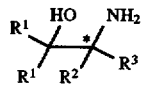  (V)

where $R^1$, $R^2$, $R^3$ and the asterisk have the above-defined meanings) or an acid addition salt thereof. Such a compound (V) may be acylated with a reagent such as trichloroacetyl chloride, e.g. in the presence of a weak base such as pyridine, to yield a compound of formula (VI)

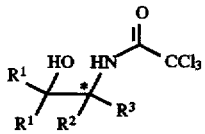  (VI)

(where $R^1$, $R^2$ and $R_3$ are as hereinbefore defined) Treatment of such a compound (VI) with base, e.g. with an inorganic base such as potassium carbonate in a polar organic solvent such as ethanol, induces elimination of the trichloromethyl group and cyclisation to yield a compound of formula (I) in which X and X' represent oxygen. Appropriate analogous techniques may be used to prepare corresponding compounds in which X and/or X' represent sulphur or a group NR (where R is as hereinbefore defined).

It will be appreciated that reactive substituents such as amino, carboxy and hydroxy groups present in either of $R^2$ and $R^3$ should desirably be protected, e.g. using conventional protecting groups such as are known in the art, during reaction sequences such as are described above.

The use of, for example, an appropriately protected serine derivative (IV) to yield a compound (I) in which, after deprotection, $R^2$ represents a hydroxymethyl group and $R^3$ represents a hydrogen atom provides a useful route to compounds (I) in which $R^2$ is a group —CH₂OP (where P is as hereinbefore defined), for example by reaction with an appropriate etherifying or esterifying agent to yield a compound in which P is an etherifying or esterifying hydroxyl protecting group, or with an appropriately activated polymer system, for example with a chloromethylated divinylbenzene-crosslinked polystyrene such as Merrifield's polymer, e.g. in the presence of base and a catalytic amount of a crown ether, to yield a compound in which P is a polymeric group.

The following non-limitative examples serve to illustrate the invention.

Formulae for Examples

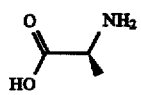  (1)

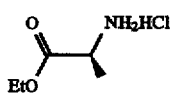  (2)

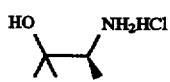  (3)

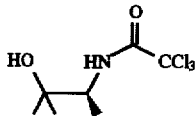  (4)

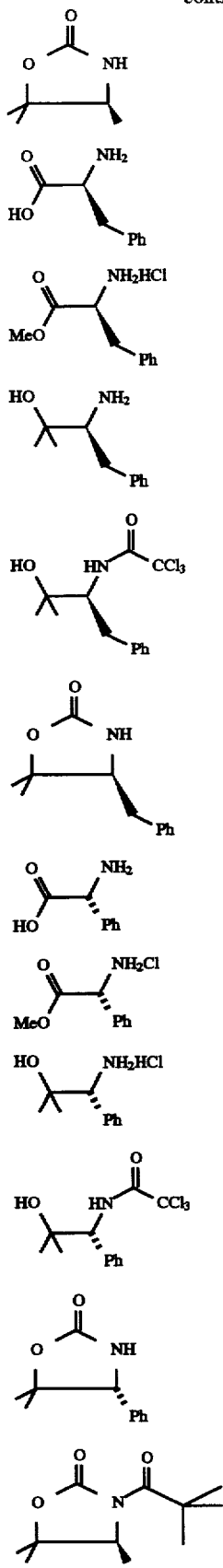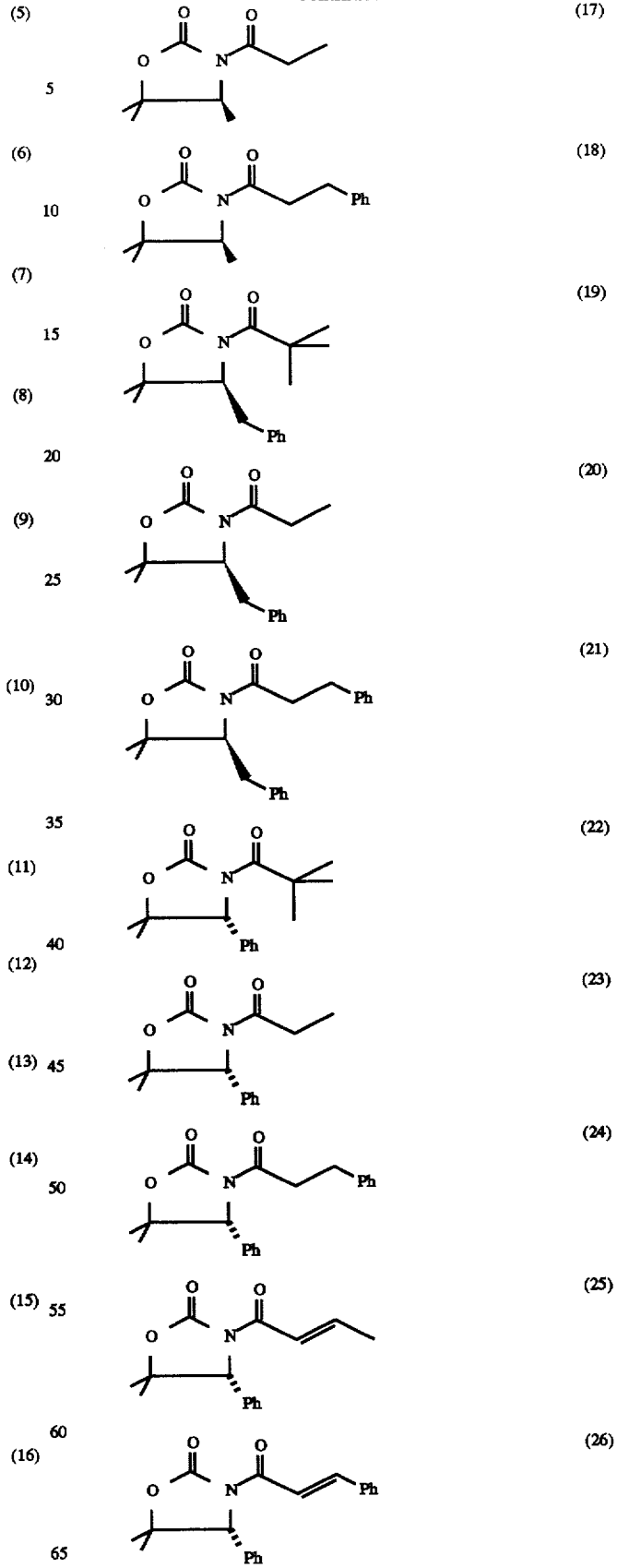

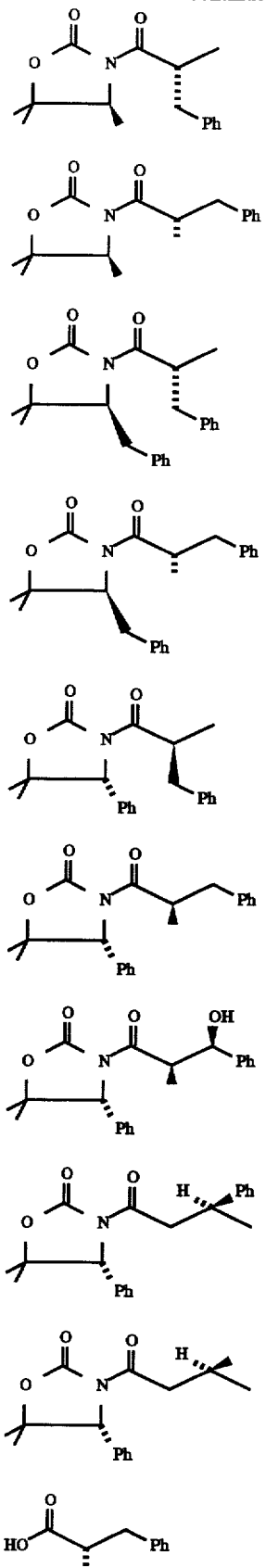
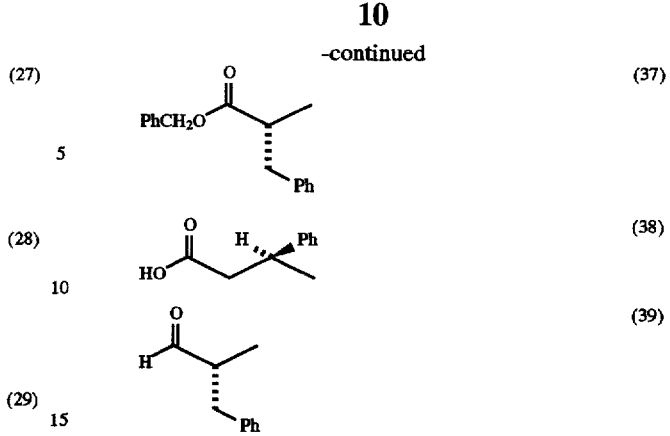

Preparation of chiral auxiliaries

EXAMPLE 1 a) L-Alanine ethyl ester hydrochloride (2)

Hydrogen chloride gas was bubbled into a suspension of L-alanine (1) (100 g, 1.12 mol) in dry ethanol (800 ml) and the solution was refluxed for 2 hours. After concentration in vacuo the compound was recrystallised from ethanol-diethyl ether giving the title ester (2) (168.2g, 98%) as a white solid. $\delta_H$ (200 MHz; $D_2O$) 1.11 (3H, t, J=7.1, $CH_2CH_3$), 1.37 (3H, d, J=7.4, $CHCH_3$), 4.03 (1H, q, J=7.2, $CHCH_3$), 4.09 (2H, q, J=7.2, $CH_2CH_3$), 4.16 (2H, s, $NH_2$); $\delta_C$ (125 MHz; $D_2O$) 13.98 ($CH_3$), 15.90 ($CH_3$), 49.65 (CH), 64.29 ($CH_2$), 171.57 (CO).

b) (S)-3-Amino-2-methyl-2-butanol (3)

L-Alanine ethyl ester hydrochloride (2) (3g, 19.53 mmol) was added in portions, during 15 minutes, to a solution of methylmagnesium iodide [prepared from methyl iodide (7.3 ml, 117.2 mmol)] in diethyl ether (114 ml) and refluxed for 30 minutes. After decomposition with water, the ethereal solution was decanted, and the volatile bases were then removed from the residual sludge of magnesium hydroxide by the addition of sodium hydroxide. The crude product was obtained by filtration through celite, distillation in steam, and neutralisation of the distillate with hydrochloric acid followed by evaporation. The compound was purified by solution in hot butan-1-ol and precipitation with ether giving the title compound (3) (1.447 g, 53%) as a white solid; mp 135° C.; $\delta_H$ (200 MHz; $D_2O$) 1.19 (3H, s, $(CH_3)_2COH$), 1.24 (3H, d, J=7, $CH_3CH$), 1.28 (3H, s, $(CH_3)_2COH$), 4.78 (2H, S, $NH_2$); $\delta_C$ (125 MHz; $D_2O$) 13.14 ($CH_3$), 21.68 ($CH_3$), 25.90 ($CH_3$, 55.85 (CH), 70.67 (C).

c) N-[(1S)-2-Hydroxy-1,2-dimethylpropyl]-2,2,2-trichloroethanamide (4)

To a solution of (3) (1.193 g, 8.56 mmol) at 0° C. in pyridine (24 ml) was added trichloroacetyl chloride (1.05 ml, 9.41 mmol). After stirring at this temperature for 10 minutes, the reaction mixture was stirred overnight at room temperature. The reaction was quenched by the addition of saturated aqueous sodium chloride solution, after which the product was extracted with dichloromethane and the combined organic extracts were washed with hydrochloric acid (1M). Concentration in vacuo and purification by flash column chromatography using 30% ethyl acetate/40–60 petroleum ether as eluant furnished the title compound (4) (1.992 g, 94%) as an oil; $v_{max}$ ($CH_2Cl_2$) 1713 cm$^{-1}$; $[\alpha]_D^{24}$ (c 1.2 in $CHCl_3$)=+6.3; (Found: C, 33.71; H, 5.12; N, 5.72.

$C_7H_{12}Cl_3NO_2$ requires C, 33.83; H, 4.87; N, 5.64%); $\delta_H$ (200 MHz; $CDCl_3$) 1.21 (3H, d, J=3.4, $CH_3CH$), 1.25 (3H, s, $C(CH_3)_2$), 1.26 (3H, s, $C(CH_3)_2$), 2.31 (1H, s, OH), 3.82 (1H, dq, J=6.7 and 8.8, $CHCH_3NH$), 7.1 (1H, s, NH); $\delta_C$ (125 MHz; $CDCl_3$) 14.89 ($CH_3$), 26.68 ($CH_3$), 27.56 ($CH_3$), 55.19 (CH), 72.01 (C), 92.82 ($CCl_3$), 161.56 (CO); m/z ($CI^+$, $NH_3$) 248 ($M^+$).

d) (S)-4,5,5-Trimethyloxazolidin-2-one (5)

To a solution of (4) (1.964 g, 7.92 mmol) in ethanol (140 ml) was added potassium carbonate (0.547 g, 3.96 mmol) and the solution was refluxed for 30 minutes. After concentration in vacuo, dichloromethane was added and the mixture was washed with saturated aqueous sodium chloride solution. Concentration in vacuo gave crude crystalline solid which was purified by recrystallisation in toluene/60–80 petroleum ether giving the title compound (5) (0.968 g, 95%); mp 60° C.; $v_{max}$ ($CDCl_3$) 1758 $cm^{-1}$; $[\alpha]_D^{24}$ (c 2 in $CHCl_3$)=+1.2; (Found: C, 56.13; H, 8.85; N, 10.79. $C_6H_{11}NO_2$ requires C, 55.80; H, 8.58; N, 10.84%); $\delta_H$ (500 MHz; $CDCl_3$) 1.12 (3H, d, J=6.6, $CHCH_3$), 1.27 (3H, s, $C(CH_3)_2$), 1.39 (3H, s, $C(CH_3)_2$), 3.59 (1H, J=6.5, $CHCH_3$), 7.27 (1H, s, NH); $\delta_C$ (125 MHz; $CDCl_3$) 16.07 ($CH_3$), 21.46 ($CH_3$), 27.14 ($CH_3$), 57.12 (CH), 83.50 (C), 159.00 (CO); m/z ($CI^+$, $NH_3$) 130 ($M^+$+1).

EXAMPLE 2 a) L-Phenylalanine methyl ester hydrochloride (7)

To a stirred solution of L-phenylalanine (6) (40 g, 242 mmol) in methanol (193 ml) at −10° C. was added thionyl chloride (19.45 ml, 266 mmol) and the solution was refluxed for 2 hours. After concentration in vacuo the compound was recrystallised from methanol-diethyl ether mixture giving the title ester (7) (52.23 g, 100%); $\delta_H$ ($D_2O$; 200 MHz) 2.95–3.18 (2H, m, $CH_2CH$), 3.62 (3H, s, $CH_3$), 4.21 (1H, dd, J=6.1 and 7.4, $CH_2CH$), 4.59 (2H, s, $NH_2$), 7.06–7.27 (5H, m, ArCH).

b) (3S)-3-Amino-2-methyl-4-phenylbutan-2-ol (8)

L-Phenylalanine methyl ester hydrochloride (7) (8 g, 37.09 mmol) was added in portions, during 15 minutes, to a solution of methylmagnesium iodide [prepared from methyl iodide (13.76 ml, 222.6 mmol)] in diethyl ether (304 ml) and refluxed for 6 hours. To promote hydrolysis, a saturated solution of ammonium chloride (19.38 g, 370.9 mmol) in water (70 ml) was added dropwise with vigorous stirring. The insoluble product was filtered off through celite, and the organic layer was separated and dried with sodium sulphate. Concentration in vacuo gave a colourless oil. The aqueous layer was made alkaline by addition of aqueous ammonia. The product was extracted with diethyl ether, dried with sodium sulphate and concentrated in vacuo. The oily residues were then combined and distilled giving the title compound (8) (2.686 g, 41%).

c) N-[(1S)-1-Benzyl-2-hydroxy-2-methylpropyl]-2,2,2-trichloroethanamide (9)

To a solution of (8) (2.573 g, 14.37 mmol) in pyridine (50 ml) at 0° C. was added trichloroacetyl chloride (1.93 ml, 17.25 mmol). After stirring at this temperature for 10 minutes, the reaction mixture was stirred overnight at room temperature. The reaction was quenched by the addition of saturated aqueous sodium chloride solution, after which the product was extracted with dichloromethane and the combined organic extracts were washed with hydrochloric acid (1M). Concentration in vacuo and purification by flash column chromatography using 30% ethyl acetate/40–60 petroleum ether as eluant furnished the title compound (9) (4.093 g, 88%) as a solid; mp 88° C.; $v_{max}$ ($CDCl_3$) 1713 $cm^{-1}$; $[\alpha]_D^{24}$ (c 0.8 in $CHCl_3$)=−26.8; (Found: C, 48.32; H, 4.61; N, 4.13. $C_{13}H_{16}Cl_3NO_2$ requires C, 48.16; H, 4.97; N, 4.32%); $\delta_H$ (300 MHz; $CDCl_3$) 1.32 (3H, S, $C(CH_3)_2$), 1.40 (3H, s, $C(CH_3)_2$), 1.91 (1H, s, OH), 2.75 (1H, dd, J=10.9 and 14.2, $CH_2Ph$), 3.20 (1H, dd, J=4.04 and 14.2, $CH_2$ Ph), 4.04–4.13 (1H, m, $CHCH_2$), 6.80 (1H, d, J=9.3, NH); $\delta_C$ (125 MHz; $CDCl_3$) 27.18 ($CH_3$), 27.74 ($CH_3$), 35.43 ($CH_2$), 60.25 (CH), 72.92 (C), 93.00 ($CCl_3$), 126.89 (CH), 128.78 (CH), 129.33 (CH), 137.66 (C), 162.07 (CO); m/z ($CI^+$, $NH_3$) 324 ($M^+$).

d) (S)-4-Benzyl-5,5-dimethyloxazolidin-2-one (10)

To a solution of (9) (4.093 g, 12.63 mmol) in ethanol (280 ml) was added potassium carbonate (0.872 g, 6.32 mmol) and the solution was refluxed for 30 minutes. After concentration in vacuo, dichloromethane was added and the mixture was washed with saturated aqueous sodium chloride solution. Concentration in vacuo gave crude crystalline solid which was purified by recrystallisation in diethyl ether/40–60 petroleum ether to give the title compound (10) (2.003 g, 77%); mp 59° C.; $v_{max}$($CHCl_3$) 1753 $cm^{-1}$; $[\alpha]_D^{25}$ (c 0.6 in $CHCl_3$)=−103.5; (Found: C, 70.52; H. 7.09; N, 6.52. $C_{12}H_{15}NO_2$ requires C, 70.22; H, 7.37; N, 6.82%); $\delta_H$ (200 MHz; $CDCl_3$) 1.45 (6H, s, $C(CH_3)_2$), 2.64–2.88 (2H, m, $CH_2Ph$), 3.72 (1H, dd, J=4.5 and 10.9, $CHCH_2$), 5.45 (1H, s, NH), 7.18–7.38 (5H, m, ArCH); $\delta_C$ (125 MHz; $CDCl_3$) 21.82 ($CH_3$), 27.42 ($CH_3$), 36.99 ($CH_2$), 63.08 (CH), 83.28 (C), 127.32 (CH), 129.08 (CH), 129.22 (CH), 137.19 (C), 158.47 (CO); m/z ($CI^+$, $NH_3$) 206 ($M^+$+1).

e) (S)-4-Benzyl-5,5-dimethyloxazolidin-2-one (10)

To a solution of (8) (16.27 g, 90.9 mmol) in dichloromethane (1 l) was added carbonyl diimidazole (17.69 g, 109.1 mmol) and the reaction mixture was refluxed for 2 hours. The reaction was quenched with hydrochloric acid (1M) and the product extracted repeatedly with dichloromethane. The combined organic extracts were dried over magnesium sulphate. After concentration in vacuo the residue was purified by flash column chromatography using 40% ethyl acetate/40–60 petroleum ether as eluant to give the title compound (10) (17.89 g, 96%).

EXAMPLE 3 a) D-Phenylglycine methyl ester hydrochloride (12)

To a stirred solution of D-phenylglycine (11) (20 g, 132 mmol) in methanol (100 ml) at −10° C. was added thionyl chloride (10.62 ml, 146 mmol) and the solution was refluxed for 2 hours. After concentration in vacuo the product was recrystallised from methanol-diethyl ether mixture to give the title compound (12) (26.6 g, 100%); $\delta_H$ ($D_2O$; 200 MHz) 2.95–3.18 (2H, m, $CH_2CH$), 3.62 (3H, s, $CH_3$), 4.21 (1H, dd, J=6.1 and 7.4, $CH_2CH$), 4.59 (2H, s, $NH_2$), 7.06–7.27 (5H, m, ArCH).

b) (1R)-1-Amino-2-methyl-1-phenyl-2-propanol (13)

D-Phenylglycine methyl ester hydrochloride (12) (5 g, 24.83 mmol) was added in portions, during 15 minutes, to a solution of methylmagnesium iodide [prepared from methyl iodide (9.28 ml, 148.97 mmol)] in diethyl ether (190 ml) and stirred for 3 hours. To promote hydrolysis, a saturated solution of ammonium chloride was added dropwise with vigorous stirring. The insoluble product was filtered off through celite, and the organic layer was separated and dried with sodium sulphate. Concentration in vacuo gave a colourless oil. The aqueous layer was made alkaline by addition of aqueous ammonia. The product was extracted with diethyl ether, dried with sodium sulphate and concentrated in vacuo. The oily residues were then combined and distilled to give the title compound (13) (1.66 g, 41%) as a solid which was recrystallised from 40–60 petroleum-ether; mp 49° C.; $[\alpha]_D^{25}$ (c 1 in CHCl$_3$) –23.2; (Found: C, 72.83; H, 9.05; N, 8.30. C$_{10}$H$_{15}$NO requires C, 72.69; H, 9.15; N, 8.48%); $\delta_H$ (200 MHz; CDCl$_3$) 1.04 (3H, s, C(CH$_3$)$_3$), 1.21 (3H, s, C(CH$_3$)$_3$), 2.16 (3H, s, NH$_2$ and OH), 3.39 (1H, s, CHPh), 7.27–7.34 (5H, m, ArCH); $\delta_C$ (125 MHz; CDCl$_3$) 24.69 (CH$_3$), 27.55 (CH$_3$), 64.54 (CH), 72.26 (C), 127.48 (ArCH), 128.05 (ArCH), 128.23 (ArCH), 142.82 (C) ; m/z (CI$^+$, NH$_3$) 166 (M$^+$+1).

c) N-[(1R)-2-Hydroxy-2-methyl-1-phenylpropyl]-2,2,2-trichloroethanamide (14)

To a solution of (13) (1.413 g, 8.56 mmol) in pyridine (24 ml) at 0° C. was added trichloroacetyl chloride (1.05 ml, 9.41 mmol). After stirring at this temperature for 10 minutes the reaction mixture was stirred overnight at room temperature. The reaction was quenched by the addition of saturated aqueous sodium chloride solution, after which the product was extracted with dichloromethane and the combined organic extracts were washed with hydrochloric acid (1M). Concentration in vacuo and purification by flash column chromatography using 30% ethyl acetate/40–60 petroleum ether as eluant furnished the title compound (14) (1.782 g, 65%) as a solid which was recrystallised from ether/40–60 petroleum ether; mp 97° C.; $v_{max}$ (CHCl$_3$) 1716 cm$^{-1}$; $[\alpha]_D^{24}$ (c 1 in CHCl$_3$)=–55.5; (Found: C, 46.41; H, 4.26; N, 4.49. C$_{12}$H$_{14}$Cl$_3$NO$_2$ requires C, 46.40; H, 4.54; N, 4.51%); $\delta_H$ (200 MHz; CDCl$_3$) 1.06 (3H, s, C(CH$_3$)$_2$), 1.39 (3H, s, C(CH$_3$)$_2$), 1.94 (1H, s, OH), 4.70 (1H, d, J=8.5, CHCH), 7.29–7.39 (5H, m, ArCH); $\delta_C$ (125 MHz; CDCl$_3$) 27.70 (CH$_3$), 27.86 (CH$_3$), 63.06 (CH), 75.52 (C), 92.97 (CCl$_3$), 128.13 (ArCH), 128.35 (ArCH), 128.71 (ArCH), 137.88 (C), 161.51 (CO); m/z (CI$^-$, NH$_3$) 310 (M$^+$).

d) (R)-4-Phenyl-5,5-dimethyloxazolidin-2-one (15)

To a solution of (14) (1.655 g, 5.33 mmol) in ethanol (140 ml) was added potassium carbonate (0.369 g, 2.67 mmol) and the solution was refluxed for 30 minutes. After concentration in vacuo, dichloromethane was added and the mixture was washed with saturated aqueous sodium chloride solution. Concentration in vacuo gave crude crystalline solid which was purified by recrystallisation in ethyl acetate/ pentane to give the title compound (15) (0.939 g, 92%); mp 149° C.; $v_{max}$ (CHCl$_3$) 1753 cm$^{-1}$; $[\alpha]_D^{25}$ (c 0.5 in CHCl$_3$) =–77.6; (Found: C, 69.32; H, 7.05; N, 7.38. C$_{11}$H$_{13}$NO$_2$ requires C, 69.09; H, 6.85; N, 7.33%); $\delta_H$ (200 MHz; CDCl$_3$) 0.93 (3H, s, C(CH$_3$)$_2$), 1.61 (3H, s, C(CH$_3$)$_2$), 4.66 (1H, s, CHPh), 6.25 (1H, s, NH), 7.25–7.44 (5H, m, ArCH); $\delta_C$ (125 MHz; CDCl$_3$ 23.53 (CH$_3$), 28.04 (CH$_3$), 65.93 (CH), 84.63 (C), 126.67 (ArCH), 128.72 (ArCH), 128.93 (ArCH), 137.16 (C), 159.75 (CO) ; m/z (CI$^+$, NH$_3$) 192 (M$^+$+1).

e) (R)-4-Phenyl-5,5-dimethyloxazolidin-2-one (15)

To a solution of (13) (1.30 g, 7.89 mmol) in dichloromethane (100 ml) was added carbonyl diimidazole (1.534 g, 9.47 mmol) and the reaction mixture was refluxed for 2 hours. The reaction was quenched with hydrochloric acid (1M) and the product extracted repeatedly with dichloromethane. The combined organic extracts were dried over magnesium sulphate. After concentration in vacuo the residue was purified by flash column chromatography using 40% ethyl acetate/40–60 petroleum ether as eluant to give the title compound (15) (1.24 g, 82%).

N-acylation of chiral auxiliaries

General procedure

The auxiliary was dissolved in tetrahydrofuran and cooled to –78° C. Butyllithium as a 1.0–1.6M solution in hexane (1.01 eq.) was then added dropwise and the mixture stirred at this temperature for 30 minutes. Freshly distilled acid chloride (1.1 eq.) was then added and the mixture was left for 30 minutes at this temperature and then at room temperature (monitoring by thin layer chromatography). The reaction mixture was then poured into pH 7 phosphate buffer solution and the product was extracted with dichloromethane and washed with saturated aqueous solution bicarbonate solution. The combined organic extracts were washed with saturated aqueous sodium chloride solution and dried over magnesium sulphate. After concentration in vacuo the residue was purified by recrystallisation or flash column chromatography.

EXAMPLE 4

(S)-3-(2',2'-Dimethyl-1'-oxopropyl)-4,5,5-trimethyloxazolidin-2-one (16)

Reaction of the auxiliary (5) (0.180 g, 1.40 mmol) in solution in tetrahydrofuran (3 ml) at –78° C. with butyllithium (1.4M, 1 ml, 1.41 mmol) and pivaloyl chloride (0.190 ml, 1.55 mmol) for 30 minutes and then at room temperature for 1 hour with work-up and recrystallisation at ca –10° C. from 60–80 petroleum ether furnished the title compound (16) as a solid (0.276 g, 93%); $v_{max}$ (CH$_2$Cl$_2$) 1683 and 1775 cm$^{-1}$; $[\alpha]_D^{24}$ (c 1 in CHCl$_3$)=+51.3; (Found: C, 62.25; H, 9.09; N, 6.45. C$_{11}$H$_{19}$NO$_3$ requires C, 61.95; H, 8.98; N, 6.57%); $\delta_H$ (CDCl$_3$; 300 MHz) 1.20 (3H, d, J=6.5, CH$_3$CH), 1.31 (9H, s, C(CH$_3$)$_3$), 1.33 (3H, s, C(CH$_3$)$_2$), 1.37 (3H, s, C(CH$_3$)$_2$), 4.11 (1H, q, J=6.5, CHCH$_3$) ; $\delta_C$ (125 MHz; CDCl$_3$) 14.33 (CH$_3$), 21.41 (CH$_3$), 26.31 (CH$_3$), 27.22 (CH$_3$), 41.60 (CH$_3$), 60.92 (CH), 81.01 (C), 151.75 (CO), 179.08 (CO); m/z (CI$^+$, NH$_3$) 214 (M$^+$+1).

EXAMPLE 5

(S)-3-(1'-Oxopropyl)-4,5,5-trimethyloxazolidin-2-one (17)

Reaction of the auxiliary (5) (0.577 g, 4.47 mmol) in solution in tetrahydrofuran (20 ml) at –78° C. with butyllithium (1.6M, 2.82 ml, 4.52 mmol) and propionyl chloride (0.427 ml, 4.92 mmol) for 30 minutes and then at room temperature for 1 hour, with work-up and recrystallisation from 40–60 petroleum ether furnished the title compound (17) as a solid (0.780 g, 94%); mp 86° C.; v. (CHCl$_3$) 1703 and 1781 cm$^{-1}$; $[\alpha]_D$25 (c 0.9 in CHCl$_3$)=+58.1; (Found: C, 58.08; H, 7.85; N, 7.53. C$_9$H$_{15}$NO$_3$ requires C, 58.36; H, 8.16; N, 7.56%); $\delta_H$ (CDCl$_3$; 300 MHz) 1.05 (3H, t, J=7.4, CH$_3$CH$_2$), 1.18 (3H, d, J=6.5, CHCH$_3$), 1.31 (3H, s, C(CH$_3$)$_2$), 1.34 (3H, s, C(CH$_3$)$_2$), 2.82 (2H, q, J=7.3, CH$_2$CH$_3$), 4.09 (1H, q, J=6.5, CHCH$_3$); $\delta_C$ (125 MHz; CDCl$_3$) 8.08 (CH$_3$), 14.41 (CH$_3$), 21.30 (CH$_3$), 27.58 (CH$_3$), 29.09 (CH$_2$), 58.72 (CH), 81.36 (C), 152.91 (CO), 174.49 (CO) ; m/z (CI$^+$, NH$_3$) 186 (M$^+$+1).

EXAMPLE 6

(S)-3-(1'-Oxopropyl-3'-phenyl)-4,5,5-trimethyloxazolidin-2-one (18)

Reaction of the auxiliary (5) (0.466 g, 3.61 mmol) in solution in tetrahydrofuran (15 ml) at −78° C. with butyllithium (1.5M, 2.43 ml, 3.65 mmol) and hydrocinnamoyl chloride (0.590 ml, 3.97 mmol) for 30 minutes and then at room temperature for 1 hour, with work-up and recrystallisation at ca. −10° C. from 40–60 petroleum ether furnished the title compound (18) as a solid (0.797 g, 85%); mp 58° C.; $v_{max}$ (CDCl$_3$) 1698 and 1773 cm$^{-1}$; $[\alpha]_D^{22}$ (c 0.8 in CHCl$_3$) =+48.9; (Found: C, 68.73; H, 7.47; N, 5.12. C$_{15}$H$_{19}$NO$_3$ requires C, 68.94; H, 7.33; N, 5.36%); $\delta_H$ (CDCl$_3$; 200 MHz) 1.26 (3H, d, J=7.4, CH$_3$CH), 1.38 (6H, s, C(CH$_3$)$_2$), 2.98 (2H, m, CH$_2$CH$_2$), 3.28 (2H, m, CH$_2$CH$_2$), 4.16 (1H, q, J=6.5, CHCH$_3$), 7.26 (5H, m, ArCH); $\delta_C$ (125 MHz; CDCl$_3$) 14.62 (CH$_3$), 21.52 (CH$_3$), 27.73 (CH$_3$), 30.46 (CH$_2$), 37.22 (CH$_2$), 58.88 (CH), 81.46 (C), 126.19 (CH), 128.43 (CH), 140.48 (C), 152.67 (CO), 172.73 (CO); m/z (CI$^+$, NH$_3$) 262 (M$^+$+1).

EXAMPLE 7

(S)-3-(2',2'-Dimethyl-1'-oxopropyl)-4-benzyl-5,5-dimethyloxazolidin-2-one (19)

Reaction of the auxiliary (10) (0.085 g, 0.415 mmol) in solution in tetrahydrofuran (2 ml) at −78° C. with butyllithium (1.6M, 0.262 ml, 0.419 mmol) and pivaloyl chloride (0.056 ml, 0.456 mmol) for 30 minutes and then at room temperature for 2 hours with work-up and flash column chromatography using 30% ethyl acetate/40–60 petroleum ether furnished the title compound (19) as an oil (0.104 g, 87%); $v_{max}$ (CDCl$_3$) 1742 cm$^{-1}$; $\delta_H$ (CDCl$_3$; 300 MHz) 1.30 (3H, s, C(CH$_3$)$_2$), 1.34 (6H, s, C(CH$_3$)$_2$), 1.35 (3H, s, C(CH$_3$)$_2$), 2.86 (1H, dd, J=9.3 and 14.2, CH$_2$Ph), 3.05 (1H, dd, J=4.1 and 14.2, CH$_2$Ph), 4.53 (1H, dd, J=4.2 and 9.3, CHCH$_2$), 7.18–7.28 (5H, m, ArCH); $\delta_C$ (125 MHz; CDCl$_3$) 22.10 (CH$_3$), 26.29 (CH$_3$), 28.07 (CH$_3$), 35.24 (CH$_2$), 41.68 (C), 65.47 (CH), 81.80 (C), 126.94 (CH), 128.76 (CH), 129.38 (CH), 137.19 (C), 152.03 (CO), 179.49 (CO); m/z (CI$^+$, NH$_3$) 290 (M$^+$+1).

EXAMPLE 8

(S)-3(1'-Oxopropyl)-4-benzyl-5,5-dimethyloxazolidin-2-one (20)

Reaction of the auxiliary (10) (0.8 g, 3.90 mmol) in solution in tetrahydrofuran (27 ml) at −78° C. with butyllithium (1.3M, 3.03 ml, 3.94 mmol) and propionyl chloride (0.373 ml, 4.29 mmol) for 30 minutes and then at room temperature overnight with work-up and recrystallisation from pentane gave the title compound (20) as a solid (0.870 g, 85%); mp 61° C.; $v_{max}$ (CHCl$_3$) 1773 and 1702 cm$^{-1}$; $[\alpha]_D^{25}$ (c 1 in CHCl$_3$)=−42.5; (Found: C, 69.06; H, 7.43; N, 5.21. C$_{15}$H$_{19}$NO$_3$ requires C, 68.94; H, 7.33; N, 5.36%); $\delta_H$ (CDCl$_3$; 200 MHz) 1.13 (3H, t, J=7.36, CH$_2$CH$_3$), 1.35 (3H, s, C(CH$_3$)$_2$), 1.36 (3H, s, C(CH$_3$)$_2$), 2.81–2.98 (2H, m, CH$_2$Ph and CH$_2$CH$_3$), 3.14 (1H, dd, J=4.0 and 14.4, CH$_2$Ph), 4.50 (1H, dd, J=4.0 and 9.6, CHCH$_2$), 7.18–7.34 (5H, m, ArCH); $\delta_C$ (125 MHz; CDCl$_3$) 8.20 (CH$_3$), 22.15 (CH$_3$), 28.43 (CH$_3$), 29.23 (CH$_2$), 35.24 (CH$_2$), 63.46 (CH), 82.20 (C), 126.96 (CH), 128.82 (CH), 129.26 (CH), 137.26 (C), 152.93 (CO), 174.53 (CO); m/z (CI$^+$, NH$_3$) 262 (M$^+$+1).

EXAMPLE 9

(S)-3-(1'-Oxopropyl-3'-phenyl)-4-benzyl-5,5-dimethyloxazolidin-2-one (21)

Reaction of the auxiliary (10) (0.3 g, 1.46 mmol) in solution in tetrahydrofuran (6 ml) at −78° C. with butyllithium (1.3M, 1.14 ml, 1.48 mmol) and hydrocinnamoyl chloride (0.238 ml, 1.60 mmol) for 20 minutes and then at 0° C. for 45 minutes with work-up and flash column chromatography gave the title compound (21) as an oil (0.481 g, 98%); $v_{max}$ (CHCl$_3$) 1774 and 1698 cm$^{-1}$; $[\alpha]_D^{24}$ (c 0.5 in CHCl$_3$)=−25.4; $\delta_H$ (CDCl$_3$; 200 MHz) 1.33 (3H, s, C(CH$_3$)$_2$), 1.38 (3H, s, C(CH$_3$)$_2$), 2.81–3.33 (6H, m, CH$_2$CH$_2$Ph and CHCH$_2$Ph), 4.53 (1H, dd, J=4.0 and 9.1, CHCH$_2$), 7.17–7.37 (10H, m, ArCH); $\delta_C$ (125 MHz; CDCl$_3$) 22.19 (CH$_3$), 28.40 (CH$_3$), 30.37 (CH$_2$), 35.24 (CH$_2$), 37.16 (CH$_2$), 63.47 (CH), 82.33 (C), 126.45 (CH), 127.04 (CH), 128.49 (CH), 128.72 (CH), 128.89 (CH), 129.29 (CH), 137.19 (C), 140.71 (C), 152.91 (CO), 172.97 (CO); m/z (CI$^+$, NH$_3$) 338 (M$^+$+1).

EXAMPLE 10

(R)-3-(2',2'-Dimethyl-1'-oxopropyl)-4-phenyl-5,5-dimethyloxazolidin-2-one (22)

Reaction of the auxiliary (15) (0.155 g, 0.81 mmol) in solution in tetrahydrofuran at −78° C. with butyllithium (1.0M, 0.819 ml, 0.821 mmol) and pivaloyl chloride (0.110 ml, 0.89 mmol) for 30 minutes and then at room temperature for 3 hours with work-up and flash column chromatography using 20% ethyl acetate/40–60 petroleum ether as eluant furnished the title compound (22) as an oil (0.128 g, 57%); $v_{max}$ (CHCl$_3$) 1687 and 1775 cm$^{-3}$; $[\alpha]_D^{25}$ (c 0.4 in CHCl$_3$) =−60.3; (Found: C, 69.94; H, 7.84; N, 4.93. C$_{16}$H$_{21}$NO$_3$ requires C, 69.80; H, 7.69; N, 5.09%); $\delta_H$ (CDCl$_3$; 300 MHz) 0.98 (3H, s, C(CH$_3$)$_2$), 1.39 (9H, s, C(CH$_3$)$_3$), 1.60 (3H, s, C(CH$_3$)$_2$), 5.11 (1H, s, CHPh), 7.14–7.37 (5H, m, ArCH; $\delta_C$ (125 MHz; CDCl$_3$) 23.66 (CH$_3$), 26.20 (CH$_3$), 28.68 (CH$_3$), 41.63 (C), 69.03 (CH), 81.80 (C), 126.10 (ArCH), 128.44 (ArCH), 128.85 (ArCH), 136.80 (C), 153.50 (CO), 178.00 (CO); m/z (CI$^+$, NH$_3$) 276 (M$^+$+1).

EXAMPLE 11

(R)-3-(1'-Oxopropyl)-4-phenyl-5,5-dimethyloxazolidin-2-one (23)

Reaction of the auxiliary (15) (0.250 g, 1.31 mmol) in solution in tetrahydrofuran (10 ml) at −78° C. with butyllithium (1.6M, 0.826 ml, 1.32 mmol) and propionyl chloride (0.125 ml, 1.34 mmol) for 30 minutes and then at room temperature for 2 hours, with work-up and flash column chromatography using 30% ethyl acetate/40–60 petroleum ether as eluant funished the title compound (23) as a solid (0.302 g, 93%); mp 60° C.; $v_{max}$ (CDCl$_3$) 1708 and 1775 cm$^{-1}$; $[\alpha]_D^{25}$ (c 1 in CHCl$_3$)=−47.8; (Found: C, 67.86; H, 6.65; N, 5.35. C$_{14}$H$_{17}$NO$_3$ requires C, 68.00; H, 6.93; N, 5.66%); $\delta_H$ (CDCl$_3$; 200 MHz) 0.98 (3H, s, C(CH$_3$)$_2$), 1.12 (3H, t, J=7.4, CH$_3$CH$_2$), 1.59 (3H, s, C(CH$_3$)$_2$), 3.00 (2H, q, J=7.4, CH$_2$CH$_3$), 5.07 (1H, s, CHPh), 7.12–7.37 (5H, m, ArCH); $\delta_C$ (125 MHz; CDCl$_3$) 8.06 (CH$_3$), 23.56 (CH$_3$), 28.91 (CH$_3$), 29.30 (CH$_2$), 66.95 (CH), 82.48 (C), 126.48 (ArCH), 128.78 (ArCH), 129.08 (ArCH), 136.67 (C), 153.57 (CO), 174.13 (CO); m/z (CI$^+$, NH$_3$) 247 (M$^+$+1).

EXAMPLE 12

(R)-3-(1'-Oxopropyl-3'-phenyl)-4-phenyl-5,5-dimethyloxazolidin-2-one (24)

Reaction of the auxiliary (15) (0.200 g, 1.05 mmol) in solution in tetrahydrofuran (10 ml) at −78° C. with butyllithium (1.6M, 0.66 ml, 1.06 mmol) and hydrocinnamoyl chloride (0.170 ml, 1.15 mmol) for 30 minutes and then at room temperature for 2 hours, with work-up and flash column chromatography using 30% ethyl acetate/40–60 petroleum ether as eluant furnished the title compound (24) as a solid (0.316 g, 94%); mp 85°–86° C.; $v_{max}$ (CDCl$_3$) 1703 and 1780 cm$^{-1}$; $[\alpha]_D^{25}$ (c 1 in CHCl$_3$)=−38.3; $\delta_H$ (CDCl$_3$; 200 MHz) 0.99 (3H, s, C(CH$_3$)$_2$), 1.57 (3H, s, C(CH$_3$)$_2$), 2.98 (2H, t, J=2.9, CH$_2$CH$_2$Ph), 3.37 (2H, t, J=1.6 (CH$_2$CH$_2$Ph), 5.10 (1H, s, ClPh), 7.12–7.41 (10H, m, ArCH); $\delta_C$ (125 MHz; CDCl$_3$) 23.71 (CH$_3$), 28.91 (CH$_3$), 30.29 (CH$_2$), 37.30 (CH$_2$), 66.94 (CH), 81.48 (C), 126.22 (ArCH), 128.48 (ArCH), 128.54 (ArCH), 128.90 (ArCH), 136.33 (C), 140.47 (C), 153.22 (CO), 172.20 (CO); m/z (CI$^+$, NH$_3$) 324 (M$^+$+1).

EXAMPLE 13

(4R)-3-[2(E)-butenoyl]-4-phenyl-5,5-dimethyloxazolidin-2-one (25)

Reaction of the auxiliary (15) (0.416 g, 2.19 mmol) in solution in tetrahydrofuran (10 ml) at −78° C. with butyl-lithium (1.3M, 1.69 ml, 2.20 mmol) and crotonyl chloride (0.229 ml, 2.40 mmol) for 30 minutes and then at room temperature for 2 hours, with work-up and flash column chromatography using 20% ethyl acetate/40–60 petroleum ether as eluant furnished the title compound (25) as a solid (0.564 g, 100%) ; mp 104° C.; $v_{max}$ (CDCl$_3$) 1687 and 1769 cm$^{-1}$; $[\alpha]_D^{24}$ (c 1 in CDCl$_3$)=−82.6; (Found: C, 69.60; H, 6.64; N, 5.35. C$_{15}$H$_{17}$NO$_3$ requires C, 69.48; H, 6.61; N, 5.40%); $\delta_H$ (CDCl$_3$; 200 MHz) 0.99 (3H, s, C(CH$_3$)$_2$), 1.60 (3H, s, C(CH$_3$)$_2$), 1.93 (3H, d, J=5.4, CH$_3$CHCH), 5.13 (1H, s, CHPh), 7.02–7.40 (7H, m, ArCH and CH$_3$CH═CH); $\delta_C$ (125 MHz; CDCl$_3$) 18.39 (CH$_3$), 23.60 (CH$_3$), 28.81 (CH$_3$), 67.09 (CH), 82.87 (C), 122.14 (CH), 126.08 (CH), 126.19 (CH), 128.71 (CH), 129.08 (CH), 136.61 (C), 147.31 (CH), 153.50 (CO), 165.07 (CO); m/z (CI$^+$, NH$_3$) 260 (M$^+$+1).

EXAMPLE 14

(4R)-3-[3-Phenyl-2(E)-propenoyl]-4-phenyl-5,5-dimethyloxazolidin-2-one (26)

Reaction of the auxiliary (15) (0.300 g, 1.57 mmol) in solution in tetrahydrofuran (10 ml) at −78° C. with butyl-lithium (1.5M, 1.06 ml, 1.59 mmol) and cinnamoyl chloride (0.228 ml, 1.73 mmol) for 10 minutes and then at room temperature for 2 hours, with work-up and flash column chromatography using 20% ethyl acetate/40–60 petroleum ether as eluant furnished the title compound (26) as a solid (0.503 g, 99%) which was recrystallised from ethyl acetate/40–60 petroleum ether; mp 149° C.; $v_{max}$ (CDCl$_3$) 1682 and 1771 cm$^{-1}$; $[\alpha]_D^{26}$ (c 1 in CHCl$_3$)=+26.0; (Found: C, 74.79; H, 5.94; N, 4.28. C$_{20}$H$_{19}$NO$_3$ requires C, 74.75; H, 5.96; N, 4.36%); $\delta_H$ (CDCl$_3$; 200 MHz) 1.04 (3H, s, C(CH$_3$)$_2$), 1.65 (3H, s, C(CH$_3$)$_2$), 5.24 (1H, s, CHPh), 7.20–7.64 (10H, m, ArCH), 7.80 (1H, d, J=15.8, CH═CHPh), 8.07 (1H, d, J=15.8, CH═CHPh); $\delta_C$ (125 MHz; CDCl$_3$) 23.78 (CH$_3$), 28.99 (CH$_3$), 67.24 (CH), 82.47 (C), 117.17 (CH), 126.37 (CH), 128.48 (CH), 128.90 (CH), 130.70 (CH), 134.54 (C), 136.38 (C), 146.53 (CH), 153.33 (CO), 165.04 (CO); m/z (CI$^+$, NH$_3$) 322 (M$^+$+1)

Electrophilic substitution of N-acylated auxiliaries

General procedure

To a solution of the N-acylated auxiliary in tetrahydrofuran cooled to 0° C. was added a solution of lithium diisopropylamine (1.1 eq.). The mixture was stirred at this temperature for 1 hour and then quenched by addition of the electrophile (3 eq.). The mixture was stirred at this temperature (monitoring by thin layer chromatography until reaction was complete). The reaction mixture was poured into pH 7 phosphate buffer solution and repeatedly extracted with dichloromethane. The combined organic extracts were washed with saturated aqueous sodium chloride solution and dried over magnesium sulphate. After concentration in vacuo the residue was purified by column chromatography to give the desired product. The recorded diastereoisomeric excesses were measured by integration of the signals at $\delta_H$ (CDCl$_3$; 500 MHz) 1.01–1.16 (CH$_3$ and CH$_3$CH) (Examples 15 and 16), $\delta_H$ (CDCl$_3$; 500 MHz) 4.43–4.46 (CHCH$_2$Ph) (Examples 17 and 18) and $\delta_H$ (CDCl$_3$; 500 MHz) 4.90–5.1 (CHPh) Examples 19 and 20) from the complementary diastereoisomers in the crude residue.

EXAMPLE 15

(2'R,4S)-3-(1'-Oxopropyl-2'-phenylmethyl)-3,5,5-trimethyloxazolidin-2-one (27)

To a solution of (17) (0.158 g, 0.85 mmol) in tetrahydrofuran (6 ml) at 0° C. was added a solution of lithium diisopropylamine (0.5M as a solution in tetrahydrofuran, 1.88 ml, 0.94 mmol). The resulting enolate was stirred at 0° C. for 20 minutes before quenching by addition of benzyl bromide (0.304 ml, 2.56 mmol). The mixture was then stirred at 0° C. for a further 2 hours. After work up and concentration in vacuo, purification by column chromatography using 30% ethyl acetate/40–60 petroleum ether as eluant furnished the title compound (27) as an oil (0.200 g, 85%) with a diastereoisomeric excess of 90%; $v_{max}$ (CDCl$_3$) 1697 and 1770 cm$^{-1}$; (Found: C, 70.08; H, 7.99; N, 5.03. C$_{16}$H$_{21}$NO$_3$ requires C, 69.79; H, 7.69; N, 5.09%); $\delta_H$ (CDCl$_3$; 200 MHz) 1.08 (3H, d, J=6.4, CH$_3$CH), 1.16 (3H, d, J=6.8, CH$_3$CH), 1.32 (3H, s, C(CH$_3$)$_2$), 1.40 (3H, s, C(CH$_3$)$_2$), 2.65 (1H, dd, J=7.8 and 13.3, CHCH$_2$Ph), 3.08 (1H, dd, J=7.1 and 13.2, CHCH$_2$Ph), 4.04–4.11 (2H, m, CH$_3$CH and CH$_3$CH), 7.15–7.31 (5H, m, ArCH); $\delta_C$ (125 MHz; CDCl$_3$) 14.21 (CH$_3$), 16.43 (CH$_3$), 21.36 (CH$_3$), 27.57 (CH$_3$), 39.35 (CH), 39.86 (CH$_2$), 58.93 (CH), 81.21 (C), 126.45 (CH), 128.44 (CH), 129.47 (CH), 139.40 (C), 152.69 (CO), 177.34 (CO); m/z (CI$^+$, NH$_3$) 276 (M$^+$+1).

EXAMPLE 16

(2'S,4S)-3-(1'-Oxopropyl-2'-phenylmethyl)-4,5,5-trimethyloxazolidin-2-one (28)

To a solution of (18) (0.586 g, 2.25 mmol) in tetrahydrofuran (20 ml) at 0° C. was added a solution of lithium diisopropylamine (0.5M as a solution in tetrahydrofuran, 4.94 ml, 2.47 mmol). The resulting enolate was stirred at 0° C. for 1 hour before quenching by addition of methyl iodide (0.420 ml, 6.74 mmol). The mixture was then stirred at 0° C. for a further 30 minutes. After work up and concentration in vacuo, purification by column chromatography using 30% ethyl acetate/40–60 petroleum ether as eluant furnished the title compound (28) as a solid (0.506 g, 82%) with a diastereoisomeric excess of 85%; recrystallisation in pentane gave a single diastereoisomer; mp 69° C.; $v_{max}$ (CHCl$_3$) 1695 and 1776 cm$^{-1}$; $[\alpha]_D^{24}$(c 1 in CHCl$_3$)=+102.2; (Found: C. 70.74; H, 8.03; N, 5.09. C$_{16}$H$_{21}$NO$_3$ requires C, 69.79; H, 7.69; N, 5.09%); $\delta_H$ (CDCl$_3$; 200 MHz) 1.12 (3H, s, C(CH$_3$)$_2$), 1.23 (6H, t, J=6.5, CH$_3$CH and CH$_3$CH), 1.35 (3H, s, C(CH$_3$)$_2$), 2.80 (1H, dd, J=7.1 and 13.2, CHCH$_2$Ph), 3.02 (1H, dd, J=8.1 and 13.3, CHCH$_2$Ph), 3.98–4.22 (2H, m, CH$_3$CH and CH$_3$CH), 7.14–7.28 (5H, m, ArCH); $\delta_C$ (125

MHz; CDCl$_3$) 14.49 (CH$_3$), 17.01 (CH$_3$), 21.25 (CH$_3$), 27.16 (CH$_3$), 39.35 (CH), 39.97 (CH$_2$), 58.93 (CH), 81.28 (C), 126.49 (CH), 128.53 (CH), 129.29 (CH), 139.56 (C), 152.40 (CO), 177.19 (CO) ; m/z (CI$^+$, NH$_3$)276 (M$^+$+1).

EXAMPLE 17

(2'R,4S)-3-(1'-Oxopropyl-2'-phenylmethyl)-4-benzyl-5,5-dimethyloxazolidin-2-one (29)

To a solution of (20) (0.300 g, 1.15 mmol) in tetrahydrofuran (12 ml) at 0° C. was added a solution of lithium diisopropylamine (0.5M as a solution in tetrahydrofuran, 2.52 ml, 1.26 mmol). The resulting enolate was stirred at 0° C. for 45 minutes before quenching by addition of benzyl bromide (0.410 ml, 3.45 mmol). The mixture was then stirred at 0° C. for a further 2 hours. After work up and concentration in vacuo, purification by column chromatography using 15% ethyl acetate/40–60 petroleum ether as eluant furnished the title compound (29) as an oil (0.206 g, 51%) with a diastereoisomeric excess of 95%; $v_{max}$(CHCl$_3$) 1771 and 1698 cm$^{-1}$; (Found: C, 74.99; H, 6.86; N, 4.14. C$_{22}$H$_{25}$NO$_3$ requires C, 75.19; H, 7.17; N, 3.99%); $\delta_H$ (CDCl$_3$; 200 MHz) 1.18 (3H, d, J=6.7, CHCH$_3$), 1.33 (6H, s, C(CH$_3$)$_2$), 2.55–3.15 (4H, m, CHCH$_2$Ph and CHCH$_2$Ph), 4.09–4.20 (1H, m, CHCH$_3$), 4.50 (1H, dd, J=3.6 and 9.8, NCHCH$_2$Ph), 7.18 14 7.34 (10H, m, ArCH); $\delta_C$ (125 MHz; CDCl$_3$) 16.48 (CH$_3$), 22.28 (CH$_3$), 28.56 (CH$_3$), 34.92 (CH$_2$), 39.57 (CH), 39.97 (CH$_2$), 63.63 (CH), 81.91 (C), 126.32 (CH), 126.75 (CH), 128.31 (CH), 128.64 (CH), 129.02 (CH), 129.29 (CH), 137.00 (C), 139.17 (C), 152.34 (CO), 177.02 (CO); m/z (CI$^+$, NH$_3$) 352 (M$^+$+1).

EXAMPLE 18

(2,s,4s)-3-(1'-Oxopropyl-2-phenylmethyl)-4-benzyl-5,5-dimethyloxazolidin-2-one (30)

To a solution of (21) (0.458 g, 1.36 mmol) in tetrahydrofuran (14 ml) at 0° C. was added a solution of lithium diisoproylamine (0.5M as a solution in tetrahydrofuran, 2.98 ml, 1.50 mmol). The resulting enolate was stirred at 0° C. for 45 minutes before quenching by addition of methyl iodide (0.253 ml, 4.07 mmol). The mixture was then stirred at 0° C. for a further 1 hour. After work up and concentration in vacuo, purification by column chromatography using 15% ethyl acetate/40–60 petroleum ether as eluant furnished the title compound (30) as a solid (0.314 g, 65%) with a diastereoisomeric excess of 92% which was recrystallised from pentane; mp 93° C; $v_{max}$ (CHCl$_3$) 1771 and 1697cm$^{-1}$; (Found: C, 75.01; H, 7.06; N, 3.88%). C$_{22}$H$_{25}$NO$_3$ requires C, 75.19; H, 7.17; N, 3.99%). $\delta_H$ (CDCl$_3$; 200 MHz) 1.03 (3H, s, C(CH$_3$)$_2$), 1.18 (3H, d, J=6.8, CHCH$_3$), 1.33 (3H, s, C(CH$_3$)$_2$), 2.63–3.10 (4H, m, CHCH$_2$Ph and CHCH$_2$Ph), 4.11–4.26 (1H, m, CHCH$_3$), 4.38 (1H, dd, J=4.6 and 8.8, NCHCH$_2$Ph), 7.13–7.35 (10H, m, ArCH); $\delta_C$ (125 MHz; CDCl$_3$) 17.30 (CH$_3$), 21.95 (CH$_3$), 27.67 (CH$_3$), 35.14 (CH$_2$), 39.21 (CH), 39.87 (CH$_2$), 63.35 (CH), 82.12 (C), 126.52 (CH), 127.00 (CH), 128.57 (CH), 128.80 (CH), 129.29 (CH), 137.07 (C), 139.56 (C), 152.61 (CO), 176.90 (CO); m/z (CI$^+$, NH$_3$) 352 (M$^+$+1).

EXAMPLE 19

(2'S,4R)-3-(1'-Oxopropyl-2'-phenylmethyl)-4-phenyl-5,5-dimethyloxazolidin-2-one (31)

To a solution of (23) (0.150 g, 0.61 mmol) in tetrahydrofuran (6 ml) at 0° C. was added a solution of lithium diisopropylamine (0.5M as a solution in tetrahydrofuran, 1.34 ml, 0.67 mmol). The resulting enolate was stirred at 0° C. for 45 minutes before quenching by addition of benzyl bromide (0.218 ml, 1.82 mmol). The mixture was then stirred at 0° C. for a further 90 minutes. After work up and concentration in vacuo, purification by flash column chromatography using 10% ethyl acetate/40–60 petroleum ether as eluant furnished the title compound (31) as a solid (0.129 g, 63%) with a diastereoisomeric excess of 81%; mp 99° C.; $v_{max}$ (CDCl$_3$) 1704 and 1773 cm$^{-1}$; (Found: C, 74.43; H, 6.49; N, 3.77. C$_{21}$H$_{23}$NO$_3$ requires C, 74.75; H, 6.87; N, 4.15%) $\delta_H$ (CDCl$_3$; 200 MHz) 0.97(3H, s, C(CH$_3$)$_2$), 1.16 (3H, d, J=6.7, CH$_3$CH), 1.61 (3H, s, C(CH$_3$)$_2$), 2.51 (1H, dd, J=8.1 and 13.3, CHCH$_2$Ph), 3.14 (1H dd, J=6.7 and 13.3, CHCH$_2$Ph), 4.18–4.29 (1H, m, CH$_3$CH), 5.09 (1H, s CHPh), 6.96–7.35 (10H, m, ArCH); $\delta_C$ (125 MHz; CDCl$_3$) 16.45 (CH$_3$), 23.76 (CH$_3$), 29.03 (CH$_3$), 39.57 (CH$_3$), 67.14 (CH), 82.09 (C), 126.23 (CH), 128.32 (CH), 128.82 (CH), 129.24 (CH), 136.13 (C), 139.06 (C), 156.00 (CO), 177.00 (CO); m/z (CI$^+$, NH$_3$) 338 (M$^+$+1).

EXAMPLE 20

(2'R,4R)-3-(1'-Oxopropyl-2'-phenylmethyl)-4-phenyl-5,5-dimethyloxazolidin-2-one (32)

To a solution of (24) (0.150 g, 0.465 mmol) in tetrahydrofuran (5 ml) at 0° C. was added a solution of lithium diisopropylamine (0.5M as a solution in tetrahydrofuran, 102 ml, 0.511 mmol). The resulting enolate was stirred at 0° C. for 45 minutes before quenching by addition of methyl iodide (0.086 ml, 1.40 mmol). The mixture was then stirred at 0° C. for a further 90 minutes. After work up and concentration in vacuo, purification by flash column chromatography using 10% ethyl acetate/40–60 petroleum ether as eluant furnished the title compound (32) as a solid (0.138 g, 88%) with a diastereoisomeric excess of 81%; mp 81° C.; $v_{max}$ (CDCl$_3$) 1703 and 1773 cm$^{-3}$; (Found: C, 74.35; H, 6.69; N, 4.04. C$_{21}$H$_{23}$NO$_3$ requires C, 74.75; H, 6.87; N, 4.15%) $\delta_H$ (CDCl$_3$; 200 MHz) 0.95 (3H, s, C(CH$_3$)$_2$), 1.19 (3H, d, J=6.8 CH$_3$CH), 1.35 (3H, s, C(CH$_3$)$_2$), 2.69 (1H, dd, J=7.1 and 13.5, CHCH$_2$Ph), 3.02 (1H, dd, J=8.2 and 13.4, CHCH$_2$Ph), 4.21–4.32 (1H, m, CH$_3$CH), 4.94 (1H, s, NCHPh), 7.10–7.41 (10H, m, ArCH); $\delta_C$ (125 MHz; CDCl$_3$) 17.04 (CH$_3$), 23.45 (CH$_3$), 28.48 (CH$_3$), 39.51 (CH$_3$), 67.00 (CH), 82.29 (C), 126.38 (CH), 126.54 (CH), 128.60 (CH), 128.79 (CH), 129.12 (CH), 129.36 (CH), 136.72 (C), 139.63 (C), 153.19 (CO), 176.50 (CO); m/z (CI$^+$, NH$_3$) 338 (M$^+$+1).

EXAMPLE 21

Aldol reaction

N-[(2R,3S)-3-Hydroxy-2-methyl-3-phenylpropionyl]-4-phenyl-5,5-dimethyloxazolidin-2-one(33)

To a solution of (23) (0.060 g, 0.24 mmol) in dichloromethane (4 ml) at 0° C. was added dibutylboron triflate (1M as a solution in dichloromethane, 0.284 ml, 0.284 mmol) followed by triethylamine (0.044 ml, 0.316 mmol). The reaction mixture was cooled to −78° C. and left for 30 minutes. Freshly distilled benzaldehyde (0.027 ml, 0.276 mmol) was added and left for a further 20 minutes at this temperature and then at 0° C. for a further 2 hours. The reaction was quenched by the addition of pH 7 buffer solution and methanol/30% hydrogen peroxide (2:1). The resulting mixture was stirred for 1 hour. After concentration in vacuo the product was extracted with dichloromethane and the combined organic extracts were washed with sodium hydrogen carbonate solution, saturated aqueous sodium chloride solution and dried over magnesium sulphate. After concentration in vacuo the diastereoisomeric excess was found to be 99%. Purification by flash column chromatography using 30% ethyl acetate/40–60 petroleum ether as eluant furnished the title compound (33) as a solid (0.045 g, 53%); $\delta_H$ (CDCl$_3$; 200 MHz) 0.97 (3H, s, C(CH$_3$)$_2$), 1.18 (3H, d, J=6.9, CH$_3$CH), 1.46 (3H, s, C(CH$_3$)$_2$), 3.09 (1H, d, J=2.1, OH), 4.18–4.28 (1H, m, CHCH$_3$), 5.00 (1H, s, CHPh), 5.08 (1H, d, J=2.6, CHOH), 7.10–7.43(10H, m, ArCH); $\delta_C$ (125 MHz; CDCl$_3$) 11.06 (CH$_3$), 23.61 (CH$_3$), 28.74 (CH$_3$), 44.66 (CH), 66.89 (CH), 73.79 (CH), 82.39 (C), 126.26 (CH), 127.52 (CH), 128.26 (CH), 128.97 (CH), 136.04 (C), 141.36 (C), 152.63 (CO), 176.60 (CO).

Michael addition to N-acylated auxiliaries

EXAMPLE 22

[3(3S,4R)]-3-(3-Phenylbutanoyl)-4-phenyl-5,5-dimethyloxazolidin-2-one (34)

To cuprous bromide-dimethylsulphide (0.227 g, 1.12 mmol) in tetrahydrofuran (4 ml) and dimethylsulphide (2 ml) at –40° C. was added methylmagnesium bromide (3M as a solution in tetrahydrofuran, 2.24 ml, 2.24 mmol). The reaction mixture was stirred for 10 minutes and then warmed to –15° C. and (25) (0.193 g, 0.75 mmol) dissolved in tetrahydrofuran (3 ml) was added. After 15 minutes the reaction was quenched with saturated aqueous ammonium chloride (3 ml) and the solvents were evaporated. Water (5 ml) and ethyl acetate (15 ml) were added and the resulting suspension was filtered through glass wool. The aqueous layer was separated and the organic phase was washed with 10% aqueous ammonium hydroxide (twice), water and saturated aqueous sodium chloride solution, and then dried over magnesium sulphate. After concentration in vacuo the diastereoisomeric excess was found to be 95% by integration of the signals due to NCHPh on a 500 MHz NMR. Purification by flash column chromatography using 20% ethyl acetate/40–60 petroleum ether as eluant gave the title compound (34) as a solid (0.168 g, 67%) which was recrystallised as a single diastereoisomer; mp 114° C.; $\nu_{max}$ (CH$_2$Cl$_2$) 1704 and 1775 cm$^{-1}$; $[\alpha]_D^{28}$ (c 1 in CHCl$_3$)=–28.8; (Found: C, 74.92; H, 6.79; N, 4.12. C$_{21}$H$_{23}$NO$_3$ requires C, 74.75; H, 6.87; N, 4.15%); $\delta_H$ (CDCl$_3$; 200 MHz) 0.96 (3H, s, C(CH$_3$)$_2$), 1.30 (3H, d, J=6.8, CHCH$_3$), 1.60 (3H, s, C(CH$_3$)$_2$), 3.14 (1H, dd, J=7.7 and 15.1, CH$_2$CHPh), 3.24–3.43 (1H, m, CH$_2$CHPh), 3.54 (1H, d, J=8.4 and 15.0, CH$_2$CHPh), 5.06 (1H, s, NCHPh), 6.94–7.31 (10H, m, Ar CH); $\delta_C$ (125 MHz; CDCl$_3$) 21.88 (CH$_3$), 23.71 (CH$_3$), 28.94 (CH$_3$), 36.06 (CH), 43.22 (CH$_2$), 66.98 (CH), 82.17 (C), 126.05 (CH), 126.30 (CH), 126.90 (CH), 128.34 (CH), 128.44 (CH), 128.75 (CH), 136.01 (C), 145.56 (C), 153.10 (CO), 171.78 (CO); m/z (CI$^+$, NH$_3$) 338 (M$^+$+1).

EXAMPLE 23

[3(3R,4R)]-3-(3-Phenylbutanoyl)-4-phenyl-5,5-dimethyloxazolidin-2-one (35)

To cuprous bromide-dimethylsulphide (0.176 g, 0.86 mmol) in tetrahydrofuran (4 ml) and dimethylsulphide (2 ml) at –40° C. was added methylmagnesium bromide (3M as a solution in tetrahydrofuran 0.576 ml, 1.73 mmol). The reaction mixture was stirred for 10 minutes and then warmed to –15° C. and (26) (0.185 g, 0.58 mmol) dissolved in tetrahydrofuran (3 ml) was added. After 1 hour the reaction was quenched with saturated aqueous ammonium chloride (3 ml) and the solvents were evaporated. Water (5 ml) and ethyl acetate (15 ml) were added and the resulting suspension was filtered through glass wool. The aqueous layer was separated and the organic phase was washed with 10% aqueous ammonium hydroxide (twice), water and saturated aqueous sodium chloride solution, and then dried over magnesium sulphate. After concentration in vacuo, the diastereoisomeric excess was found to be 92% by integration of the signals due to NCHPh on a 500 MHz NMR. Purification by flash column chromatography using 20% ethyl acetate/ 40–60 petroleum ether as eluant gave the title compound (35) as a solid (0.169 g, 87%); $\nu_{max}$ (CH$_2$Cl$_2$) 1704 and 1774 cm$^{-1}$; $\delta_H$ (CDCl$_3$; 200 MHz)0.98 (3H, s, C(CH$_3$)$_2$), 1.32 (3H, d, J=6.9, CHCH$_3$), 1.43 (3H, s, C(CH$_3$)$_2$), 3.18 (1H, dd, J=6.1 and 15.6, CH$_2$CHPh), 3.33–3.43 (1H, m, CHCH$_2$Ph), 3.60 (1H, d, J=8.1 and 15.6, CH$_2$CHPh), 4.98 (1H, s, NCHPh, 7.12–7.39 (10H, m, ArCH); $\delta_C$ (125 MHz; CDCl$_3$) 22.45 (CH$_3$), 23.61 (CH$_3$), 28.66 (CH$_3$), 36.30 (CH), 43.13 (CH$_2$), 66.93 (CH), 82.36 (C), 126.41 (CH), 127.05 (CH), 128.51 (CH), 128.58(CH), 128.44 (CH), 136.34 (C), 145.68 (C), 153.27 (CO), 171.72 (CO); m/z (CI$^+$, NH$_3$) 339 (M$^+$+1).

Cleavage of acyl group from N-acylated auxiliary

General procedure

The substrate was dissolved in a mixture of tetrahydrofuran and water (3:1; v/v) and cooled to 0° C. 2 equivalents of solid lithium hydroxide were added and the mixture was stirred at 0° C. for 1 hour and then warmed to room temperature (the reaction was monitored by thin layer chromatography). An aqueous solution of sodium hydrogen carbonate was then added and the regenerated auxiliary was extracted with diethyl ether or dichloromethane. The combined organic extracts were washed with saturated aqueous sodium chloride solution and dried over magnesium sulphate. Evaporation of solvent left the auxiliaries as white solids. The aqueous phase was acidified by addition of hydrochloric acid (2M) until pH 2, and extracted with ethyl acetate to obtain the acid corresponding to the cleaved acyl group. The combined organic extracts were washed with saturated aqueous sodium chloride solution and dried over magnesium sulphate. Concentration in vacuo, and purification by chromatography using 10% ethyl acetate/40–60 petroleum ether as eluant furnished the acid.

EXAMPLE 24

Cleavage of (2'S,4S)-3-(1'-oxopropyl-2'-phenylmethyl)-4,5,5-trimethyloxazolidin-2-one (28)

Product (28) (0.218 g, 0.79 mmol) with 99% diastereoisomeric excess dissolved in tetrahydrofuran and water (3:1; v/v) (4 ml) with lithium hydroxide monohydrate (0.067 g, 1.59 mmol) furnished the auxiliary (5) (0.102 g, 100° C.) and α-methyl hydrocinnamic acid (36) (0.130 g, 100%). The enantiomeric excess of the acid was measured by addition of a half mass equivalent of R,R-diphenyldiaminoethane and deuteriated benzene (0.7 ml) and integration of the signal at $\delta_H$ (d$^6$ benzene; 500 MHz) 1.12–1.14 (3H, d, CHCH$_3$) arising from the complementary diastereoisomeric solvates. The enantiomeric excess of the acid (36) was ≧99%; $[\alpha]_D^{21}$ (c 1 in CHCl$_3$)=+30.4 [lit. $[\alpha]_D^{22}$ (c 3.28 in CHCl$_3$)=+30.1].

EXAMPLE 25

Cleavage of (S)-3-(2',2'-dimethyl-1'-oxopropyl)-4,5,5-trimethyloxazolidin-2-one (16)

To the substrate (16) (0.170 g, 0.8 mmol) dissolved in a mixture of tetrahydrofuran and water (3:1; v/v) (4 ml) at 0°

C. was added lithium hydroxide monohydrate (0.084 g, 1.99 mmol). The reaction mixture was stirred for 1 hour at this temperature and then at room temperature overnight. An aqueous solution of sodium hydrogen carbonate was then added and the auxiliary extracted with dichloromethane. The combined organic extracts were washed with saturated aqueous sodium chloride solution and dried over magnesium sulphate. Evaporation of solvent left the auxiliary (5) as a white solid (0.094 g, 91%).

EXAMPLE 26

Cleavage of (S)-3-(2',2'-dimethyl-1'-oxopropyl)-4-5,5-benzyl-5,5-dimethyloxazolidin-2-one (19)

To the substrate (19) (0.100 g, 0.35 mmol) dissolved in a mixture of tetrahydrofuran and water (3:1; v/v) (4 ml) at 0° C. was added lithium hydroxide monohydrate (0.036 g, 0.87 mmol). The reaction mixture was stirred for 1 hour at this temperature and then at room temperature overnight. An aqueous solution of sodium hydrogen carbonate was then added and the auxiliary extracted with dichloromethane. The combined organic extracts were washed with saturated aqueous sodium chloride solution and dried over magnesium sulphate. Evaporation of solvent and flash column chromatography using 40% ethyl acetate/40–60 petroleum ether as eluant gave the auxiliary (10) as a white solid (0.057 g, 82%).

EXAMPLE 27

Cleavage of (R)-3-(2',2'-dimethyl-1'-oxopropyl)-4-phenyl-5,5-dimethyloxazolidin-2-one (22)

To the substrate (22) (0.094 g, 0.34 mmol) dissolved in a mixture of tetrahydrofuran and water (3:1; v/v) (4 ml) at 0° C. was added lithium hydroxide monohydrate (0.036 g, 0.86 mmol). The reaction mixture was stirred for 1 hour at this temperature and then at room temperature overnight. An aqueous solution of sodium hydrogen carbonate was then added and the auxiliary was extracted with dichloromethane. The combined organic extracts were washed with saturated aqueous sodium chloride solution and dried over magnesium sulphate. Evaporation of solvent and flash column chromatography using 40% ethyl acetate/40–60 petroleum ether yielded auxiliary (15) as a white solid (0.056 g, 86%) after recrystallisation.

EXAMPLE 28

Cleavage of Michael adduct (34)

The adduct (34) (0.11 g, 0.40 mmol) with 99% diastereoisomeric excess dissolved in tetrahydrofuran and water (3:1; v/v) (4 ml) with lithium hydroxide monohydrate (0.034 g, 0.81 mmol) furnished the auxiliary (5) (0.074 g, 97%) and the acid (38) (0.052 g, 80%). The enantiomeric excess of the acid (38) was ≧99% (elucidated by the use of a chiral shift reagent); $[\alpha]_D^{23}$ (c 0.3 in $C_6H_6$)=+53.3 [lit. $[\alpha]_D^{20}$=−57.0 (c 9.8 in $C_6H_6$) for absolute configuration R].

EXAMPLE 29

Cleavage with lithium benzyloxide

To a solution of (29) (0.126 g, 0.359 mmol) in tetrahydrofuran (2 ml) at −78° C. was added a solution of benzyl alcohol (0.074 ml, 0.717 mmol) in butyllithium (1.5M, 0.359 ml, 0.538 mmol) prepared at 0° C. The mixture was stirred at −78° C. for 10 minutes then for a further 1 hour at 0° C. pH 7 Phosphate buffer solution was then added and the products were extracted with diethyl ether. The combined organic extracts were washed with saturated aqueous sodium chloride solution and dried over magnesium sulphate. Concentration in vacuo and purification by column chromatography using 30% ethyl acetate/40–60 petroleum ether yielded the auxiliary (10) (0.064 g, 88%) and the ester (37) (0.081 g, 89%). The enantiomeric excess of the ester (37) was measured by addition of 1 mass equivalent of tris [3-(heptafluoropropyl-hydroxymethylene)-(+)-camphorato] europium (III) derivative in $CDCl_3$ (0.7 ml), and then integration of the signal at $\delta_H$ ($CDCl_3$; 500 MHZ) 1.12–1.14 (3H, d, $CHCH_3$) arising from the complementary diastereoisomeric solvates, and was found to be 94%.

EXAMPLE 30

Cleavage of N-acyl derivative to form an aldehyde

To a solution of compound (27) (0.090 g, 0.327 mmol) in toluene (1 ml) at −78° C. was added dropwise a solution of diisobutylaluminium hydride (1.5M as a solution in toluene, 0.419 ml, 0.632 mmol). The reaction mixture was stirred for 5 minutes, saturated aqueous ammonium chloride (1.5 ml) was added, the mixture was stirred at room temperature for 15 minutes and extracted with dichloromethane. The combined organic extracts were washed with brine, dried over magnesium sulphate and concentrated in vacuo. The residue was purified by flash column chromatography using 25% ethyl acetate/40–60 petroleum ether as eluant to give the aldehyde (39) (0.041 g, 89%) and the auxiliary (5) (0.026 g, .62%). The optical purity of the aldehyde was ascertained by reduction of the aldehyde to the alcohol and formation of the Mosher's ester. $^{19}$F NMR was used to measure the diastereoisomeric excess, which indicated an enantiomeric excess of 88% for the aldehyde (39).

We claim:

1. Compounds of general formula (I):

where the two $R^1$ groups are identical $C_{1-10}$ alkyl groups or together form a $C_{3-10}$ alkylene group; $R^2$ and $R^3$ are different and are each selected from the group consisting of hydrogen atoms, optionally substituted aliphatic, cycloaliphatic, araliphatic and aromatic hydrocarbyl groups containing up to 20 carbon atoms, and groups of formula —$CH_2OP$ where P represents a hydroxyl protecting group, a crosslinked polysaccharide or a divinylbenzene-crosslinked polystyrene; X and X', which may be the same or different, are each selected from the group consisting of O, S and NR, where R represents an organic group as described above for $R^2$; and the asterisk denotes that the configurations of $R^2$ and $R^3$ are such that the compound (I) is in substantially enantiomerically pure 4R- or 4S-form.

2. Compounds as claimed in claim 1 comprising at least 95% of the 4R- or 4S- enantiomer.

3. Compounds as claimed in claim 1 wherein the two $R^1$ groups are methyl groups.

4. Compounds as claimed in claim 1 wherein $R^3$ represents a hydrogen atom.

5. Compounds as claimed in claim 1 wherein X and X' represent oxygen atoms.

6. Compounds as claimed in claim 1 wherein $R^2$ and $R^3$ when other than hydrogen are selected from optionally substituted $C_{1-10}$ alkyl, $C_{2-10}$ alkenyl, $C_{3-10}$ cycloalkyl-$C_{1-4}$ alkyl, $C_{6-12}$ aryl-$C_{1-4}$ alkyl and $C_{6-12}$ aryl groups.

7. Compounds as claimed in claim 1 wherein $R^2$ represents a methyl, isopropyl, isobutyl, sec-butyl, hydroxymethyl, 1-hydroxymethyl, mercaptomethyl, carboxymethyl, 2-carboxyethyl, carbamoylmethyl, 2-carbamoylethyl, 2-(methylthio)ethyl, 4-aminobutyl, benzyl, p-hydroxybenzyl, indol-3-ylmethyl, imidazole-4-ylmethyl or 3-guanidinopropyl.

8. The compounds (S)-4,5,5-trimethyloxazolidin-2-one; (S)-4-benzyl-5,5-dimethyloxazolidin-2-one; and (R)-4-phenyl-5,5-dimethyloxazolidin-2-one.

9. A process for the preparation of a compound of general formula (I) as defined in claim 1 which comprises (i) reacting a compound of general formula (IV)

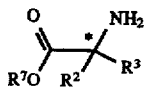 (IV)

(where $R^2$, $R^3$ and the meaning of the asterisk are as defined in claim 1 and $R^7$ represents a carboxyl protecting group) or an acid addition salt thereof with a Grignard reagent $R^1$MgX (where $R^1$ is as defined in claim 1 and X represents a halogen atom) to yield a compound of general formula (V)

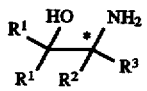 (V)

(where $R^1$, $R^2$, $R^3$ and the meaning of the asterisk are as defined in claim 1) or an acid addition salt thereof; (ii) acylating the said compound of general formula (V) or an acid addition salt thereof to yield a compound of general formula (VIa)

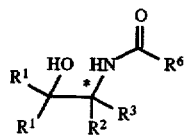 (VIa)

(where $R^1$, $R^2$, $R^3$ and the meaning of the asterisk are as defined in claim 1 and $R^6$ represents a leaving group); and (iii) cyclising said compound of general formula (VIa) to yield a compound of general formula (I).

10. Compounds of general formula (III):

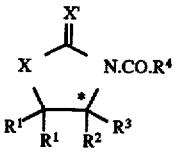 (III)

where the two $R^1$ groups are identical $C_{1-10}$ alkyl groups or together form a $C_{3-10}$ alkylene group; $R^2$ and $R^3$ are different and are each selected from the group consisting of hydrogen atoms, optionally substituted aliphatic, cycloaliphatic, araliphatic and aromatic hydrocarbyl groups containing up to 20 carbon atoms, and groups of formula —$CH_2OP$ where P represents a hydroxyl protecting group, a crosslinked polysaccharide or a divinylbenzene-crosslinked polystyrene; $R^4$ is an aliphatic, cycloaliphatic, araliphatic or aromatic hydrocarbyl group having up to 20 carbon atoms and containing a prochiral center; X and X', which may be the same or different, are each selected from the group consisting of O, S and NR, where R represents an organic group as described above for $R^2$; and the asterisk denotes that the configurations of $R^2$ and $R^3$ are such that the compound (I) is in substantially enantiomerically pure 4R- or 4S-form.

* * * * *